United States Patent
Kohayakawa

Patent Number: 6,079,830
Date of Patent: *Jun. 27, 2000

[54] EYE MEASURING APPARATUS HAVING SIGNAL PROCESSING MEANS FOR CALCULATING EYE INFORMATION

[75] Inventor: Yoshimi Kohayakawa, Yokohama, Japan

[73] Assignee: Canon Kabushiki Kaisha, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/635,788

[22] Filed: Apr. 22, 1996

Related U.S. Application Data

[63] Continuation of application No. 08/112,989, Aug. 30, 1993, abandoned.

[30] Foreign Application Priority Data

Aug. 31, 1992 [JP] Japan ............................... 4-257176

[51] Int. Cl.⁷ ..................................................... A61B 3/10
[52] U.S. Cl. ........................................... 351/211; 351/221
[58] Field of Search ................................. 351/200, 205, 351/211, 214, 221

[56] References Cited

U.S. PATENT DOCUMENTS

| | | | |
|---|---|---|---|
| 4,609,287 | 9/1986 | Kohayakawa | 356/124 |
| 4,697,895 | 10/1987 | Sekiguchi et al. | 351/243 |
| 4,820,037 | 4/1989 | Kohayakawa et al. | 351/211 |
| 5,071,245 | 12/1991 | Fukuma et al. | 351/211 |
| 5,144,346 | 9/1992 | Nakamura et al. | 351/208 |
| 5,210,555 | 5/1993 | Ishikura et al. | 351/214 X |
| 5,231,430 | 7/1993 | Kohayakawa | 351/243 |
| 5,237,351 | 8/1993 | Kohayakawa et al. | 351/243 |
| 5,280,313 | 1/1994 | Kohayakawa | 351/211 |

FOREIGN PATENT DOCUMENTS 4-30293  5/1992  Japan.

*Primary Examiner*—Hung Xuan Dang
*Attorney, Agent, or Firm*—Fitzpatrick, Cella, Harper & Scinto

[57] ABSTRACT

An eye measuring apparatus which, even if it is of the portable type in which it is difficult to maintain alignment, can effect accurate measurement without requiring a high skill of operation includes a light projecting system for projecting a light beam onto an eye to be examined, a light receiving system for detecting the reflected light from the eye to be examined by a light detecting element, and signal processing means for calculating the eye information of the eye to be examined on the basis of the detection by the light detecting element. The signal processing means is effective to sequentially monitor the output from the light detecting element and indicate eye refraction information on the basis of the detection by the light detecting element when a predetermined light reception signal is obtained.

28 Claims, 5 Drawing Sheets

EYE MEASURING APPARATUS HAVING SIGNAL PROCESSING MEANS FOR CALCULATING EYE INFORMATION

This application is a continuation of application Ser. No. 08/112,989, filed Aug. 30, 1993, now abandoned.

BACKGROUND OF THE INVENTION

1. Field of the Invention

This invention relates to an eye measuring apparatus for use in ophthalmic hospitals and opticians' stores.

2. Related Background Art

In an eye refractometer which is one type of conventional eye measuring apparatus, auto refractometers of the stationary type have come into wide use and are designed to effect measurement with the examinee's face fixed. Among such apparatuses, there is known one in which with regard to alignment, a corneal reflected light beam is monitored to thereby confirm alignment, whereafter measurement is started.

In the alignment effected with the corneal reflected light beam monitored, a light source for measurement must be turned on after the termination of the monitoring and an eye fundus reflected light beam must be accumulated on a photoelectric sensor and thus, the timing of measurement is delayed. In a portable type of apparatus, it is difficult to maintain the aligned state of an eye to be examined and the apparatus and during this delay, positional deviation may occur to make accurate measurement impossible.

SUMMARY OF THE INVENTION

It is a first object of the present invention to provide an eye measuring apparatus which, even if it is of the portable type in which it is difficult to maintain alignment, can effect accurate measurement without requiring a large amount of skill of operation of the apparatus.

It is a second object of the present invention to provide a simple eye measuring apparatus which does not particularly require a position detecting system for an eye to be examined.

Other objects of the present invention will become apparent from the following detailed description of the invention.

DESCRIPTION OF THE PREFERRED EMBODIMENTS

Figure 1:
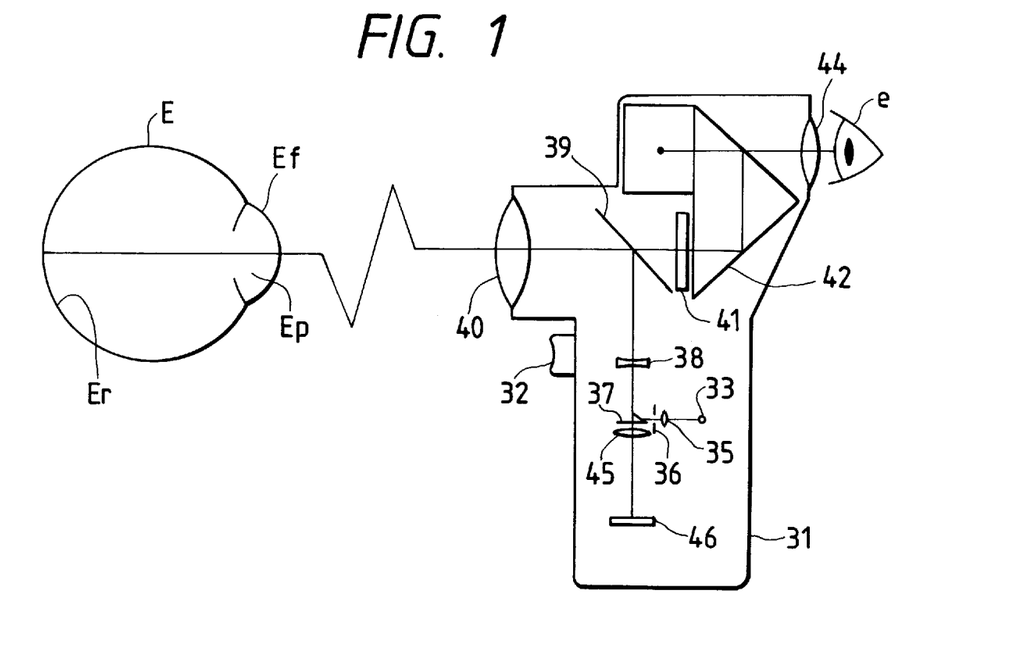
FIG. 1 shows the construction of a first embodiment of the present invention.
Figure 2:
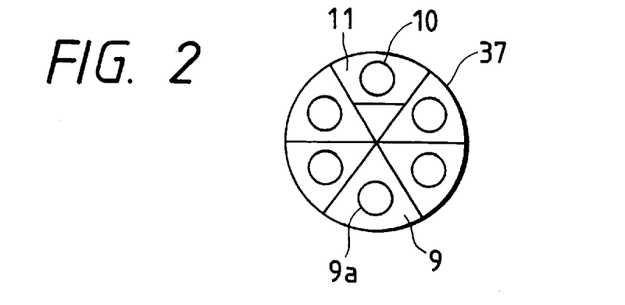
FIG. 2 is a front view of a light beam limiting member.

Referring to FIG. 1 which shows the construction of a first embodiment of the present invention, a lens 35, a small aperture stop 36, a light beam limiting member 37 the details of which are shown in FIG. 2, a concave lens 38, a dichroic mirror 39 and a convex lens 40 are disposed on an optical path leading from a light source emitting near infrared light which is provided in an apparatus provided with a grip 31 and a push button 32, to an eye E to be examined, and a focusing screen 41 provided with a split prism or a diffusing surface, a porro prism 42 and an eyepiece 44 which are disposed on an optical path behind the dichroic mirror 39. A lens 45 and a photoelectric sensor 46 comprising a two-dimensional CCD of the accumulation type are provided behind the light beam limiting member 37. The dichroic mirror 39 has a wavelength spectral characteristic of transmitting visible light therethrough and reflecting a measuring light beam which is near infrared light. The light beam limiting member 37, as shown in FIG. 2, is comprised of five wedge prisms 9 each having an opening portion 9a, and a prism 11 having a small mirror 10 fixed thereto.

Figure 4:
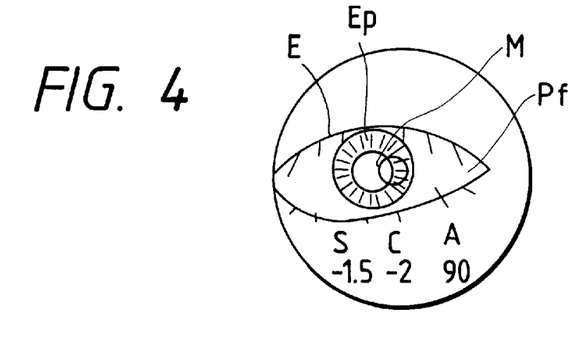
FIG. 4 illustrates an examiner's field of view.

The reflected light beam reflected by external light from the front eye part Ef of the eye E to be examined is imaged as a front eye part image Pf on the focusing screen 41 via the convex lens 40 and the dichroic mirror 39, and the front eye part image Pf shown in FIG. 4 is observed by an examiner's eye e through the porro prism 42 and the eyepiece 44.

An alignment mark M is provided on the focusing screen 41. An examiner holding the grip 31 looks into the eyepiece 44 and observes the front eye part image Pf, and the distance from the apparatus to the eye E to be examined is determined by focusing the image and the alignment mark M is aligned to the pupil Ep. When the push button 32 is depressed after the termination of the alignment, the light source 33 is turned on.

The measuring light beam from the light source 33 passes through the lens 35 and the small aperture stop 36, is reflected by the small mirror 10 of the light beam limiting member 37 and is projected in the form of a spot on the fundus Er of the eye E to be examined via the concave lens 38, the dichroic mirror 39 and the convex lens 40. The reflected light beam from the eye fundus Er returns along the same optical path, passes through the convex lens 40, the dichroic mirror 39, the concave lens 38, the opening portions 9a of the wedge prisms 9 of the light beam limiting member 37 and the lens 45 and is received as five small circular measuring light beams P1–P5 shown in FIG. 3 on the photoelectric sensor 46.

Figure 3:
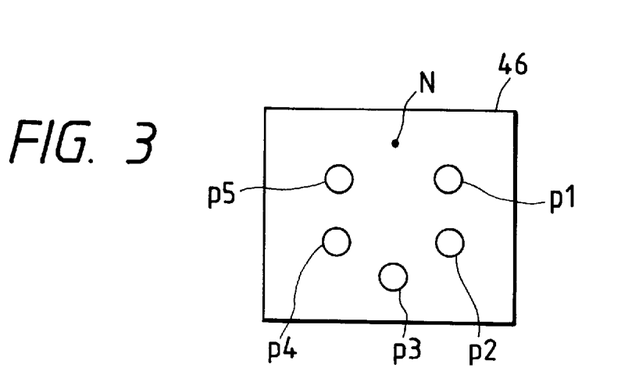
FIG. 3 illustrates a measuring light beam image on a photoelectric sensor.

The position of a point N on the photoelectric sensor 46 is in a conjugate relationship with the light source 33, and the eye refractivity in the meridian directions linking the openings 9a and 10 in the member 37 together can be found from the distance between the point N and the measuring light beam P3 and further, the eye refractivity in the respective meridian directions can be calculated from the intervals between the measuring light beams P1 and P4 and between the measuring light beams P2 and P5. From the eye refractivity in these three meridian directions, an eye refractive value comprising degree of sphericity, degree of astigmatism and astigmatic angle can be calculated. Actually, the signal of the photoelectric sensor 33 is input to a computer, not shown, whereby these calculations are effected. That is, the positions of the measuring light beams P1–P5 are analyzed by the computer, not shown, and the eye refractive value comprising the degree of sphericity S, the degree of the astigmatism C and astigmatic angle A as shown in FIG. 4 is indicated on the focusing screen 41 by an indicator, not shown, with the front eye part image Pf, and can be confirmed by the examiner's eye e.

At this time, whether the measuring light beams have reached the photoelectric sensor 46 is monitored by the output signal from the photoelectric sensor 46 being introduced into the computer at a predetermined time interval. If after the confirmation of the alignment, the signal levels of the measuring light beams P1–P5 on the photoelectric sensor 46 are above a certain predetermined level and are at the same level to some extent, it can be guessed that the measuring light beams have passed the pupil Ep without hitting the edge of the pupil. If the light beams are accumulated in the photoelectric sensor 46 for a time of the order of 10 ms, there can be obtained the necessary signal level and therefore, the signals of the photoelectric sensor 46 can be introduced into the computer at a time interval of 10 ms. When from the received light beams on the photoelectric sensor 46, it is judged that the apparatus and the eye to be examined are aligned with each other and the measuring light beams have passed the pupil Ep, the positions of these light beams are used to calculate a refractive value and indicate it.

In this case, the examinee's face and the apparatus are not fixed and therefore both of them move, but as long as the light beams pass the pupil and the edge portion of the pupil Ep does not intervene, the positions of the measuring light beams P1–P5 on the photoelectric sensor 46 will not change even if the examinee's face and the apparatus move more or less. Also, the measuring light beams P1–P5 move on the eye fundus Er and the pupil Ep with the movement of the eye E to be examined, but the reflected light beams from the eye fundus Er are always reflected in the incidence direction and therefore, no change occurs to the imaged positions of the measuring light beams P1–P5 on the photoelectric sensor 46.

Accordingly, if the light beams are not intercepted by the edge portion of the pupil Ep during the time of the order of 10 ms for which the light beams are accumulated in the photoelectric sensor 46, the conditions for the above-mentioned signal level are attained and thus, measurement becomes possible.

The above-described monitoring of the signals of the photoelectric sensor 46 in the computer can be processed within a short time because the amount calculated is small, and subsequently the calculation of the eye refractive value is effected, but a certain degree of time is necessary for this calculation and therefore, during this time, the introduction of the output signal of the photoelectric sensor 46 may be interrupted or the light source 33 may be turned off. If not an LED but a light source of high luminance such as a stroboscopic lamp or a semiconductor laser source is used as the light source 33, it will suffice for it to be turned on in the fashion of a continuous pulse at predetermined intervals.

Further, not a point-like light beam but a ring-like light beam may be projected onto the eye fundus Er, but if a light beam is projected in the form of a point onto the eye fundus Er, there is a merit that the incident light beam can be made thin and its expanse can be reduced. Also, if the measuring light beam is somewhat deviated from the optical axis of the optical system, the reflected light beam by the lens can be prevented from reaching the photoelectric sensor 46 and it can also be avoided for the lens-reflected light to prevent measurement. Where it suffices for the eye refractivity in one meridian direction to be found, a one-dimensional CCD or the like can be employed as the photoelectric sensor 46.

Figure 5:
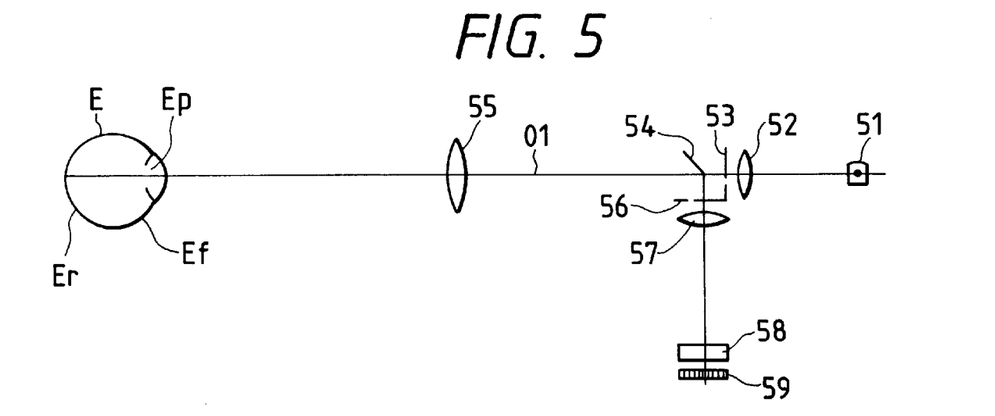
FIG. 5 shows the construction of a second embodiment of the present invention.
Figure 6:
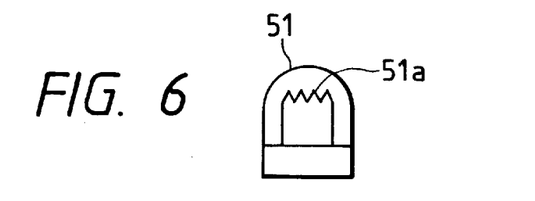
FIG. 6 shows the construction of a light source.

Referring now to FIG. 5 which shows the construction of a second embodiment of the present invention, a lens 52, a slit plate 53, a small mirror 54 and an objective lens 55 are disposed on an optical path 01 leading from a light source 51 comprising an incandescent lamp having a filament 51a as shown in FIG. 6 to the eye E to be examined, and a slit plate 56, a lens 57, a cylindrical lens 58 and a photoelectric sensor 59 comprising a one-dimensional CCD are disposed on an optical path 02 in the direction of reflection of the small mirror 54.

Figure 7:
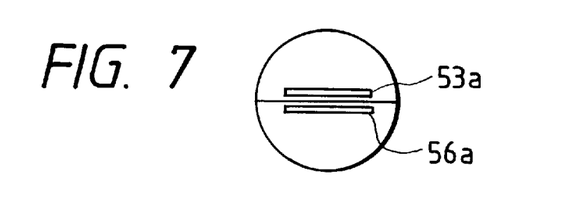
FIG. 7 shows the relation between two slit plates.

When viewed from the direction of the optical path 01, the slit plates 53 and 56 are in the relation as shown in FIG. 7, and slits 53a and 56a are formed in these slit plates, respectively, the slit 53a being on the optical path 01, the slit 56a being on the optical path 02, and both of them being disposed in a direction perpendicular to the plane of the drawing sheet of FIG. 7. Also, the light source 51 and the one-dimensional photoelectric sensor 59 are in a conjugate relationship with the eye fundus Er, and the slits 53a and 56a are in a conjugate relationship with the pupil Ep.

The light beam from the light source 51 passes through the lens 52, the slit 53a of the slit plate 53, the small mirror 54 and the objective lens 55 and is projected in the form of a slit onto the eye fundus Er. The reflected light beam from the eye fundus Er returns along the same optical path, is reflected by the small mirror 54 and is received by the one-dimensional photoelectric sensor 59 via the slit 56a of the slit plate 56, the lens 57 and the cylindrical condensing lens 58. The cylindrical lens 58 has a condensing action in a direction perpendicular to the plane of the drawing sheet of FIG. 5 and therefore causes the light beam passing through the slit 56a to be imaged in the direction on the one-dimensional photoelectric sensor 59.

Figure 8:
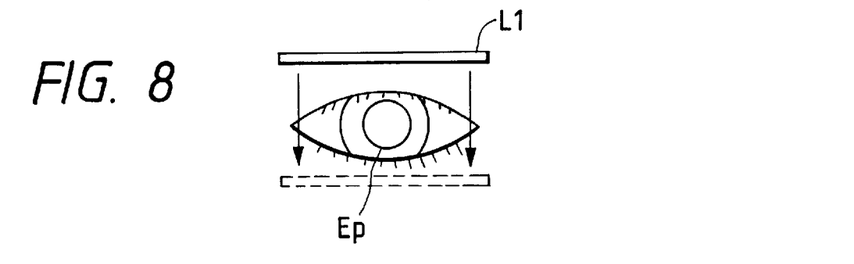
FIG. 8 illustrates the relation between a front eye part and a slit light beam image.

To effect measurement, the examiner changes the direction of the apparatus slightly so that in the front eye part Ef of the eye E to be examined, the slit light beam image L1 shown in FIG. 8 by the slit 53a of the slit plate 53 may cross the pupil Ep. When this slit light beam image L1 comes to a pupil Ep, the light beam received by the photoelectric sensor 59 has a light distribution B1 having a peak shown in FIG. 9.

Figure 9:
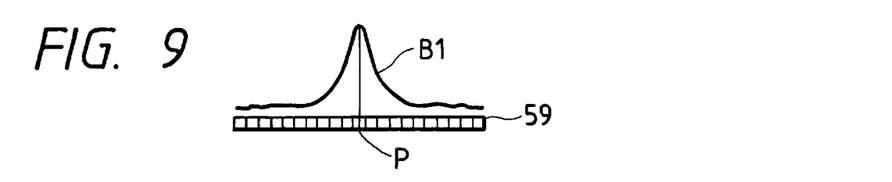
FIG. 9 is a graph showing the distribution of the quantity of received light of an eye fundus reflected light beam on a photoelectric sensor.

This light distribution B1 is read out at a predetermined time interval of e.g. 5 ms, and the peak position P is calculated and stored. This calculation and storage are effected continuously while the slit light beam image L1 crosses the pupil Ep. When the slit light beam image L1 comes to the pupil Ep, the quantity of received light becomes greatest and therefore, using suitable data selected from among the stored data, the refractivity of the eye is calculated and then indicated. This refractivity is the refractivity in the meridian direction perpendicular to slit light beam image L1 and when the apparatus is moved in a horizontal direction with the slit light beam image L1 upright, the refractivity in the horizontal meridian direction is likewise obtained. If the calculation of this refractivity is effected by the use of a so-called one-chip microcomputer driven by a battery, the entire apparatus can be made about the size of a retinoscope.

Even if the accumulation time of the eye fundus reflected light beam in the photoelectric sensor 59 is several ms, the slit light beam image L1 moves on the pupil Ep during that time. Along therewith, the light beam projected onto the eye fundus Er also moves, but if there is no aberration, the light receiving position on the photoelectric sensor 59 will not move and therefore, no problem will arise. Also, the reflection of the light beam by the objective lens 55 is not reflection on the center thereof and therefore, this reflected light does not pass through the slit 56a of the slit plate 56 to the photoelectric sensor 59 and therefore, no convenience occurs to measurement.

During the examination, it is preferable to keep a distance of the order of 50 cm between the objective lens 55 and the eye E to be examined, and the examiner instructs the examinee to look at a great distance and measurement is effected from near the direction of the visual axis. In the present embodiment, the adjustment of the distance between the eye and the apparatus is performed by judging the focus of the slit image L1 projected onto the front eye part.

Figure 10:
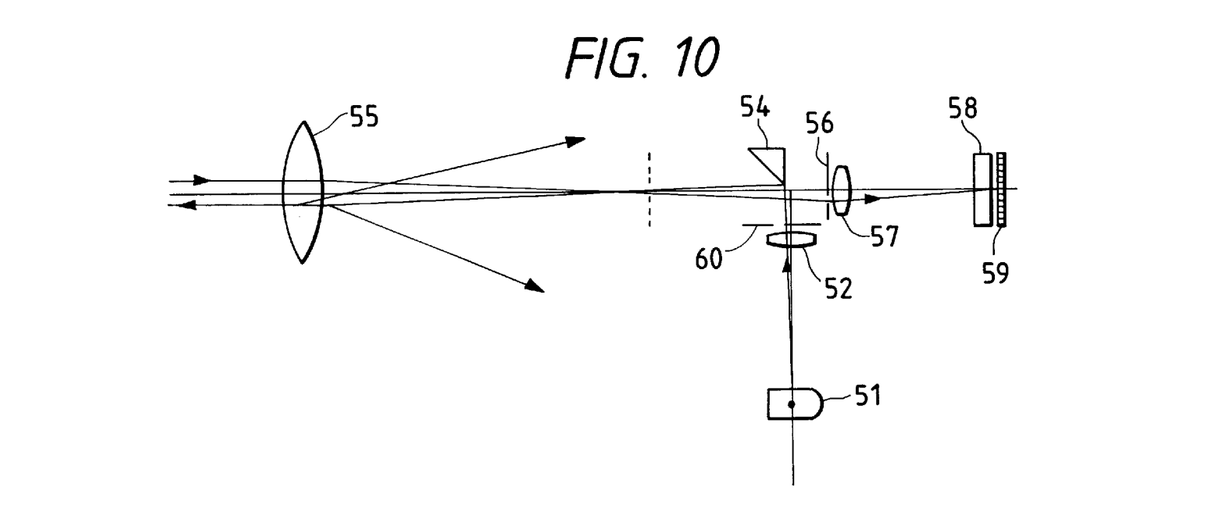
FIG. 10 shows the construction of a third embodiment of the present invention.
Figure 11:
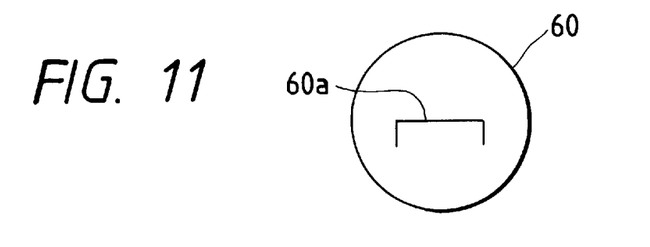
FIG. 11 is a front view of a slit plate.

FIG. 10 shows the construction of a third embodiment of the present invention. In this embodiment, the same reference numerals as those in the second embodiment designate the same members. A lens 52, a slit plate 60 formed with a U-shaped slit 60a as shown in FIG. 11, a small mirror 54 and an objective lens 55 are disposed on an optical path leading from the light source 51 to the objective lens 55, and a slit plate 56, a lens 57, a cylindrical lens 58 and a photoelectric sensor 59 are disposed on an optical path behind the small mirror 54.

Figure 12:
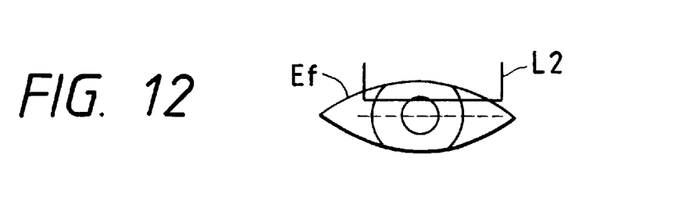
FIG. 12 illustrates the relation between the front eye part and the slit light beam image.

In the aforedescribed second embodiment, the filament 51a of the light source 51 and the slit 53a of the slit plate 53 are in a parallel positional relationship with each other and therefore, even if the distance between the eye E to be examined and the apparatus is changed, the slit light beam image L1 projected onto the front eye part Ef is scarcely blurred and thus, is difficult to focus. In this embodiment, as shown in FIG. 12, a U-shaped slit light beam image L2 passed through the slit 60a of the slit plate 60 is projected onto the front eye part Ef and therefore, the examiner can accomplish focusing while looking at the vertical slit light beam images on both ends.

For measurement, as in the second embodiment, the slit light beam image L2 can be moved so as to come to the pupil Ep, but at this time, care must be taken so that the opposite end portions of the slit light beam image L2 may not lie on the pupil Ep. The chain line in FIG. 12 represents the position of the slit 56a of the slit plate 56, and the reflected light of the slit light beam image L2 projected onto the eye fundus Er is taken out from this portion. Besides this, room light or the like enters the pupil Ep and is reflected by the eye fundus Er and is received by the photoelectric sensor 59, but this light beam is substantially uniformly distributed on the photoelectric sensor 59 and can therefore be eliminated by calculation. Also, the reflected light beam reflected by the objective lens 55 travels in the directions of arrows and therefore does not reach the photoelectric sensor 59.

Figure 13:
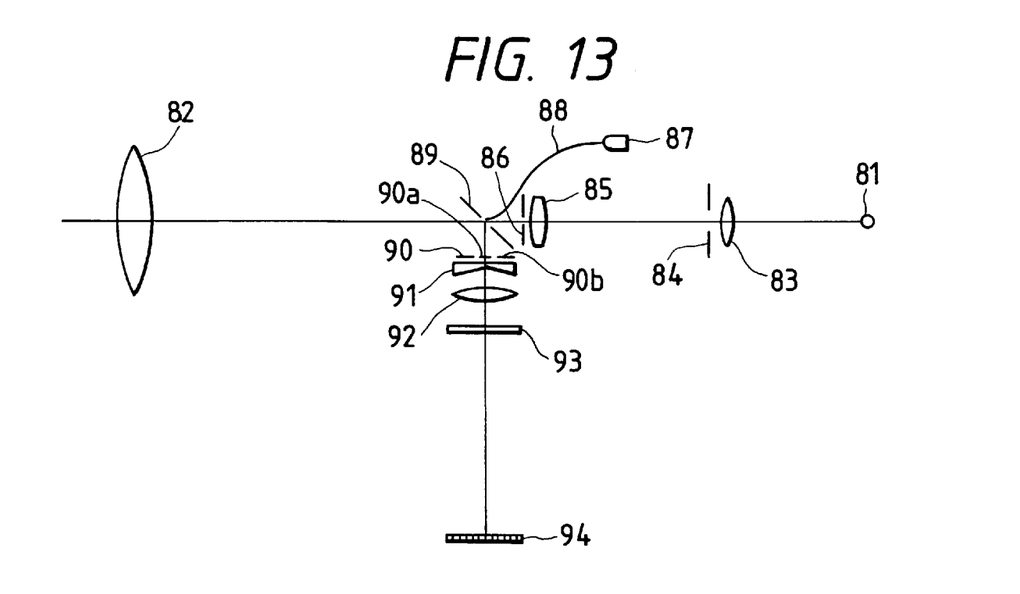
FIG. 13 shows the construction of a fourth embodiment of the present invention.
Figure 14:
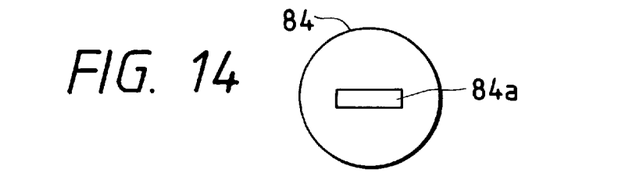
FIG. 14 is a front view of a projection stop.
Figure 15:
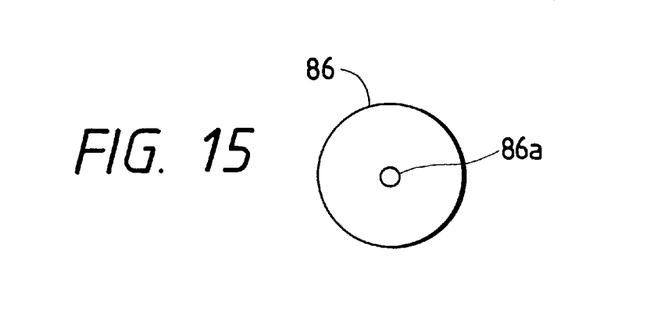
FIG. 15 is a front view of a small aperture stop.
Figure 16:
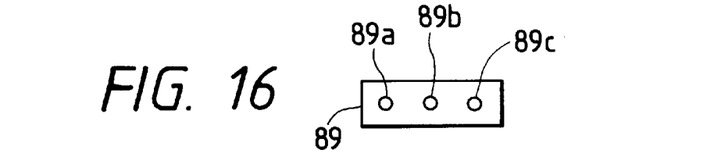
FIG. 16 is a front view of an apertured mirror.

FIG. 13 shows the construction of a fourth embodiment of the present invention. A lens 83, a projection stop 84 having an opening portion 84a as shown in FIG. 14, a lens 85, a small aperture stop 86 having an opening portion 86a as shown in FIG. 15, an apertured mirror 89 made of a metal, and an optical fiber 88 connected to a visible light LED 87 are disposed on an optical path leading from a measuring light source 81 comprising an LED or the like emitting near infrared light to an objective lens 82. The apertured mirror 89 has three opening portions 89a, 89b and 89c, as shown in FIG. 16. Further, a two-aperture stop 90, a separating prism 91 comprising two wedge prisms, a lens 92, a visible light cutting filter 93 and a photoelectric sensor 94 comprising a one-dimensional CCD are disposed on an optical path extending in the direction of reflection of the apertured mirror 89.

The small aperture stop 86 is in conjugate relationship with the pupil of the eye to be examined, and the projection stop 84 is in conjugate relationship with the eye fundus and is imaged on the focal plane of the objective lens 82 by the lens 85.

The light beam from the measuring light source 81 is projected onto the eye fundus via the lens 83, the opening portion 84a of the projection stop 84, the lens 85, the opening portion 86a of the small aperture stop 86, the central opening portion 89b of the apertured mirror 89 and the objective lens 82. The eye fundus reflected light beam travels rightward along the same optical path, is reflected by the apertured mirror 89 and is received by the photoelectric sensor 94 via the two opening portions 90a and 90b of the two-aperture stop 90, the separating prism 91 and the visible light cutting filter 93.

Figure 17:
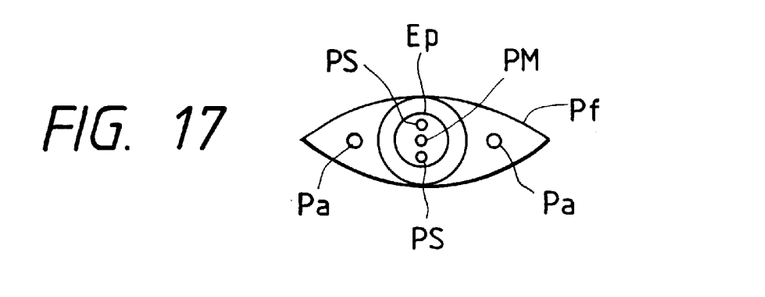
FIG. 17 is an illustration of the front eye part during measurement.

The light beam from the visible light LED 87 passes through the opening portions 89a and 89c of the apertured mirror 89 via the optical fiber 88 and is projected as an alignment image Pa for focusing onto the front eye part. FIG. 17 shows the front eye part Pf during measurement, and the examiner observes two alignment light beam images Pa projected onto the front eye part of the eye to be examined by the visible light LED 87, focuses these images on the front eye part, and effects alignment so that the center of the alignment images Pa may coincide with the center of the pupil.

Figure 18:
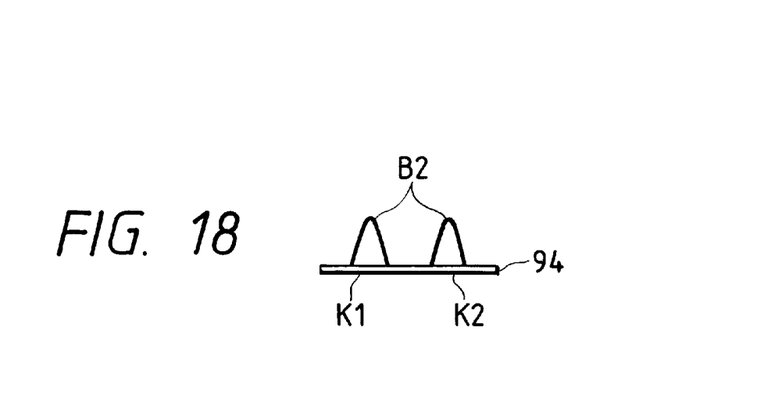
FIG. 18 is a graph showing the distribution of the quantity of received light on a photoelectric sensor.

When this alignment is completed, the position PM of the opening portion 89b of the apertured mirror 89 and the positions PS of the opening portions 90a and 90b of the two-aperture stop 90 assume the positional relation shown in FIG. 17 on the pupil Ep and therefore, the light distribution B2 of the photoelectric sensor 94 has two peaks as shown in FIG. 18. The eye refractive value is obtained from the interval between these peaks K1 and K2.

Again in this embodiment, the light reception signal of the photoelectric sensor 94 is introduced into a computer at a predetermined time interval of e.g. 5 ms, and it is monitored that the measuring light beam has been received by the photoelectric sensor 94. In this case, when the quantity-of-light distribution B2 of the photoelectric sensor 94 has two peaks of the same equal degree or higher than a predetermined level, it is judged that the light beam has entered the pupil, that is, alignment has been done, and the signal can be analyzed to find the eye refractive value.

The reflected light beam of the measuring, light beam by the objective lens 82 can be avoided by putting the stop 84 somewhat eccentric from the optical axis. The room illuminating light and the reflected light beam of the light beam from the visible LED 87 by the objective lens 82 are intercepted by the visible light cutting filter 93.

A PSD, instead of the photoelectric sensor 94, can also be used as the photoelectric sensor. In a one-dimensional PSD, there is provided a voltage ratio in which the ratio of quantity of received light is created across the PSD, and from this, the peak position of the distribution of the quantity of received light can be known. In this case, use is made of an optical system as shown in FIG. 10 wherein a light beam is received by the sensor. Further, distriction between the eye fundus reflected light beam and the room light or the like cannot be made from the quantity-of-light distribution as in a CCD and therefore, the measuring light source 81 is turned on and off so that the signal when the light source 81 is turned off may be subtracted from the signal of the quantity-of-light distribution when the light source 81 is turned on. Thereby, it is possible to eliminate the influence of the room light.

What is claimed is:

1. An eye measuring apparatus comprising:
   a light projecting system for projecting a light beam onto an eye to be examined;
   a light receiving system for detecting the reflected light from the eye to be examined by a light detecting element, said light detecting element detecting the reflected light via a fixed optical system; and
   signal processing means for calculating information of the eye to be examined on the basis of the detection by said light detecting element, said signal processing means being effective to consecutively monitor the output from said light detecting element to obtain the information, and for instructing the indicating of the information on the basis of the detection by said light detecting element when a predetermined light reception signal is obtained from said light detecting element.

2. An apparatus according to claim 1, wherein said signal processing means effects the calculation of refractive power information on the basis of the output from said light detecting element at a point in time at which said light detecting element produces a light reception signal sufficient for the calculation of the eye refractive power information of said signal processing means.

3. An apparatus according to claim 1, wherein said light detecting element detects the position of the light projected thereon.

4. An apparatus according to claim 1, wherein said light detecting element includes an accumulation type photoelectric sensor.

5. An apparatus according to claim 1, wherein said light projecting system projects the light beam through a first area of the pupil of the eye to be examined, and said light receiving system directs the light from a second area differing from said first area of the pupil of the eye to be examined to said light detecting element.

6. An apparatus according to claim 1, wherein said light projecting system projects a slit light beam.

7. An apparatus according to claim 1, wherein said signal processing means effects the calculation of the information on the basis of the detection signal of said light detecting element obtained while the light beam from said light projecting system scans the pupil of the eye to be examined.

8. An apparatus according to claim 1, wherein said light receiving system comprises a multi-aperture stop, and said signal processing means effects the calculation of the information from the positions, on said light detecting element, of a plurality of light beams obtained through said multi-aperture stop.

9. An apparatus according to claim 1, wherein said light projecting system comprises a stop having a U-shaped opening.

10. An apparatus according to claim 1, further comprising an apertured mirror wherein an optical path of said light projecting means from the eye to be examined and an optical path of said light receiving system from the eye to be examined are separated from each other by said apertured mirror.

11. An eye refraction measuring apparatus comprising:
    a light projecting system for projecting a light beam onto the fundus of an eye to be examined;
    a light receiving system for receiving the reflected light from the fundus of the eye to be examined by a light detecting element, said light detecting element detecting the reflected light via a fixed optical system; and
    signal processing means for calculating refractive information of the eye to be examined on the basis of the detection by said light detecting element to obtain the information, said signal processing means being effective to consecutively monitor the output from said light detecting element, and calculate the information on the basis of the detection by said light detecting element when a predetermined light reception signal is obtained from said light detecting element.

12. An apparatus according to claim 11, wherein said signal processing means effects the calculation of eye refraction information on the basis of the output from said light detecting element at a point in time at which said light detecting element produces a light reception signal sufficient for the calculation of the eye refraction information of said signal processing means.

13. An apparatus according to claim 11, wherein said light detecting element detects the position of the light projected thereon.

14. An apparatus according to claim 11, wherein said light detecting element includes an accumulation type photoelectric sensor.

15. An apparatus according to claim 11, wherein said light projecting system projects the light beam through a first area of the pupil of the eye to be examined, and said light receiving system directs the light from a second area differing from said first area of the pupil of the eye to be examined to said light detecting element.

16. An apparatus according to claim 11, wherein said light projecting system projects a slit light beam.

17. An apparatus according to claim 11, wherein said signal processing means effects the calculation of eye refraction information on the basis of a detection signal of said light detecting element obtained while the light beam from said light projecting system scans the pupil of the eye to be examined.

18. An apparatus according to claim 11, wherein said light receiving system comprises a multi-aperture stop, and said signal processing means effects the calculation of the eye refraction information from the positions, on said light detecting element, of a plurality of light beams obtained through said multi-aperture stop.

19. An apparatus according to claim 11, wherein said light projecting system comprises a stop having a U-shaped opening.

20. An apparatus according to claim 11, further comprising an apertured mirror wherein said light projecting system and an optical path of said light projecting means from the eye to be examined and an optical path of said light receiving system from the eye to be examined are separated from each other by said apertured mirror.

21. An eye refractive power measuring apparatus comprising:
    a light projecting system for projecting a light beam onto the fundus of an eye to be examined;
    a light receiving system for receiving the reflected light from the fundus of the eye to be examined by a light detecting element, said light detecting element detecting the reflected light via a fixed optical system; and signal processing means for calculating the eye refractive power information of the eye to be examined on the basis of the detection by said light detecting element, said signal processing means being effective to consecutively monitor the output from said light detecting element to obtain a single piece of eye refractive power information, and instructing the indicating of eye refractive power information on the basis of the detection by said light detecting element when a predetermined light reception signal is obtained from said light detecting element.

22. An apparatus according to claim 21, wherein said signal processing means calculates an eye refraction value of the eye to be examined as the eye refraction power information.

23. An eye refractive power measuring apparatus comprising:

a light projecting system for projecting a light beam onto the fundus of an eye to be examined;

a light receiving system for receiving the reflected light from the fundus of the eye to be examined by a light detecting element, said light detecting element detecting the reflected light via a fixed optical system; and signal processing means for calculating the eye refractive power information of the eye to be examined on the basis of the detection by said light detecting element, said signal processing means monitoring said light receiving system and calculating the eye refractive power information when the monitoring of said light receiving system indicates that a distribution of light received by said light receiving system achieves a predetermined level, said signal processing means instructing the indicating of the eye refractive power information after the calculation is completed.

24. An apparatus according to claim 23, wherein said signal processing means is effective to instruct display of the refractive power information as the indication.

25. An eye measuring apparatus comprising:

a light projection system for projecting light onto an eye to be examined;

a light receiving system for detecting the reflected light from the eye by light detecting means, said light detecting means detecting the reflected light via a fixed optical system;

a signal processing system for calculating information of the eye on the basis of the detection by the light detecting means, said signal processing system being effective to repeatedly monitor the output from the light detecting means to obtain the information, and for instructing the indicating of the information on the basis of the detection by said light detecting means when predetermined light reception signal is obtained from the light detecting means.

26. An eye measuring apparatus comprising:

a light projecting system for projecting a light beam onto an eye to be examined;

a light receiving system for detecting the reflected light from the eye to be examined by a light detecting element, said light detecting element detecting the reflected light via a fixed optical system; and signal processing means for calculating information of the eye to be examined on the basis of the detection by said light detecting element, said signal processing means being effective to consecutively monitor the output from said light detecting element to obtain the information, and for obtaining indication data of the information on the basis of the detection by said light detecting element when a predetermined light reception signal is obtained from said light detecting element.

27. An eye measuring apparatus comprising:

light projection means for projecting light onto an eye to be examined;

a light receiving system for detecting the reflected light from the eye by light detecting means, said light detecting means detecting the reflected light via a fixed optical system; and a signal processing system for calculating measuring information of the eye on the basis of the detection by the light detecting means, said signal processing system being effective to repeatedly monitor the output from the light detecting means, and for instructing the indicating of the measuring information on the basis of the detection by said light detecting means when a predetermined light reception signal is obtained from the light detecting means.

28. An eye measuring apparatus comprising:

light projection means for projecting light onto an eye to be examined;

a light receiving system for detecting the reflected light reflected from the eye by light detecting means, said light detecting means detecting the reflected light via a fixed optical system; and a signal processing system for processing a signal of the light detecting means, said signal processing system being effective to consecutively monitor the output of the light detecting means, and to calculate a measuring result on the basis of the detection of the light detection means and to indicate the measuring result when predetermined light is detected by the light detection means.

* * * * *

UNITED STATES PATENT AND TRADEMARK OFFICE
CERTIFICATE OF CORRECTION

PATENT NO. : 6,079,830

DATED : June 27, 2000

INVENTOR(S): Yoshimi KOHAYAKAWA

It is certified that error appears in the above-identified patent and that said Letters Patent is hereby corrected as shown below:

COLUMN 2:

Line 65, "10" should read --small mirror 10--.

COLUMN 3:

Line 7, "photoelectric sensor 33" should read --photoelectric sensor 46--.
Line 12, "the" should be deleted; and "astigmatic" should read --the astigmatic--.

COLUMN 5:

Line 15, "convenience" should read --inconvenience--.

COLUMN 6:

Line 55, "measuring," should read --measuring--.

COLUMN 7:

Line 2, "distriction" should read --distinction--.
Line 65, "means" should read --system--.

UNITED STATES PATENT AND TRADEMARK OFFICE
CERTIFICATE OF CORRECTION

PATENT NO.   :   6,079,830
DATED        :   June 27, 2000
INVENTOR(S)  :   Yoshimi KOHAYAKAWA It is certified that error appears in the above-identified patent and that said Letters Patent is hereby corrected as shown below:

COLUMN 8:

Line 55, "means" should read --system--.

COLUMN 10:

Line 1, "predetermined" should read --a predetermined--.

Signed and Sealed this

Twenty-second Day of May, 2001

Attest:

NICHOLAS P. GODICI

Attesting Officer       Acting Director of the United States Patent and Trademark Office